(12) United States Patent
Smartt et al.

(10) Patent No.: US 6,178,819 B1
(45) Date of Patent: *Jan. 30, 2001

(54) INSPECTION APPARATUS FOR EVALUATING A PARTIALLY COMPLETED WELD

(75) Inventors: Herschel B. Smartt; Eric D. Larsen; Jonn A. Johnson, all of Idaho Falls, ID (US)

(73) Assignee: Bechtel BWXT Idaho, LLC, Idaho Falls, ID (US)

(*) Notice: Under 35 U.S.C. 154(b), the term of this patent shall be extended for 0 days.

This patent is subject to a terminal disclaimer.

(21) Appl. No.: 09/196,399

(22) Filed: Nov. 19, 1998

Related U.S. Application Data

(63) Continuation of application No. 09/066,723, filed on Apr. 23, 1998, now Pat. No. 6,125,705.

(51) Int. Cl.[7] ............................. G21C 17/10; G01N 9/24
(52) U.S. Cl. .................................. 73/622; 73/598
(58) Field of Search ................ 73/618, 622, 624, 73/625, 628, 598, 627, 634, 635, 636, 639

(56) References Cited

U.S. PATENT DOCUMENTS

| | | | | |
|---|---|---|---|---|
| 4,012,946 | * | 3/1977 | Patsey | 73/627 |
| 4,368,644 | * | 1/1983 | Wentzell et al. | 73/634 |
| 4,375,165 | * | 3/1983 | Sterke | 73/622 |
| 5,423,219 | * | 6/1995 | Yaginuma et al. | 73/622 |

* cited by examiner

Primary Examiner—Max Noori
(74) Attorney, Agent, or Firm—Wells St John Roberts Gregory & Matkin

(57) ABSTRACT

An inspection apparatus for evaluating a partially completed weld is described and which is utilized in combination with an automated movable welder which moves across a supporting surface, and wherein the inspection apparatus includes a coupling member mounted on the welder; a frame member mounted on the coupling member; an ultrasonic sensor mounted on the frame member and disposed in ultrasonic sound transmitting relation relative to the partially completed weld; and a drive assembly for adjusting the position of the ultrasonic sensor relative to the partially completed weld.

51 Claims, 7 Drawing Sheets

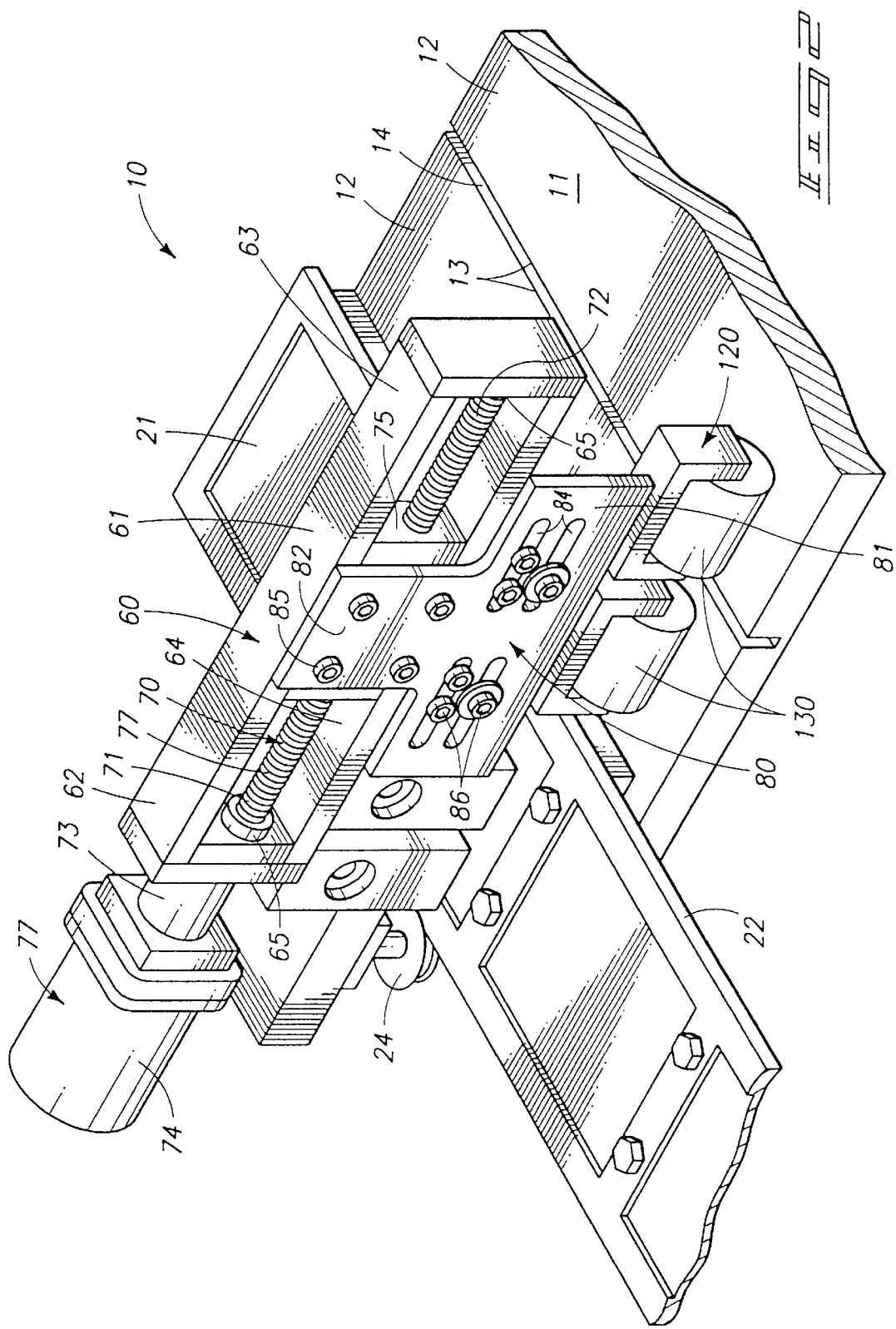

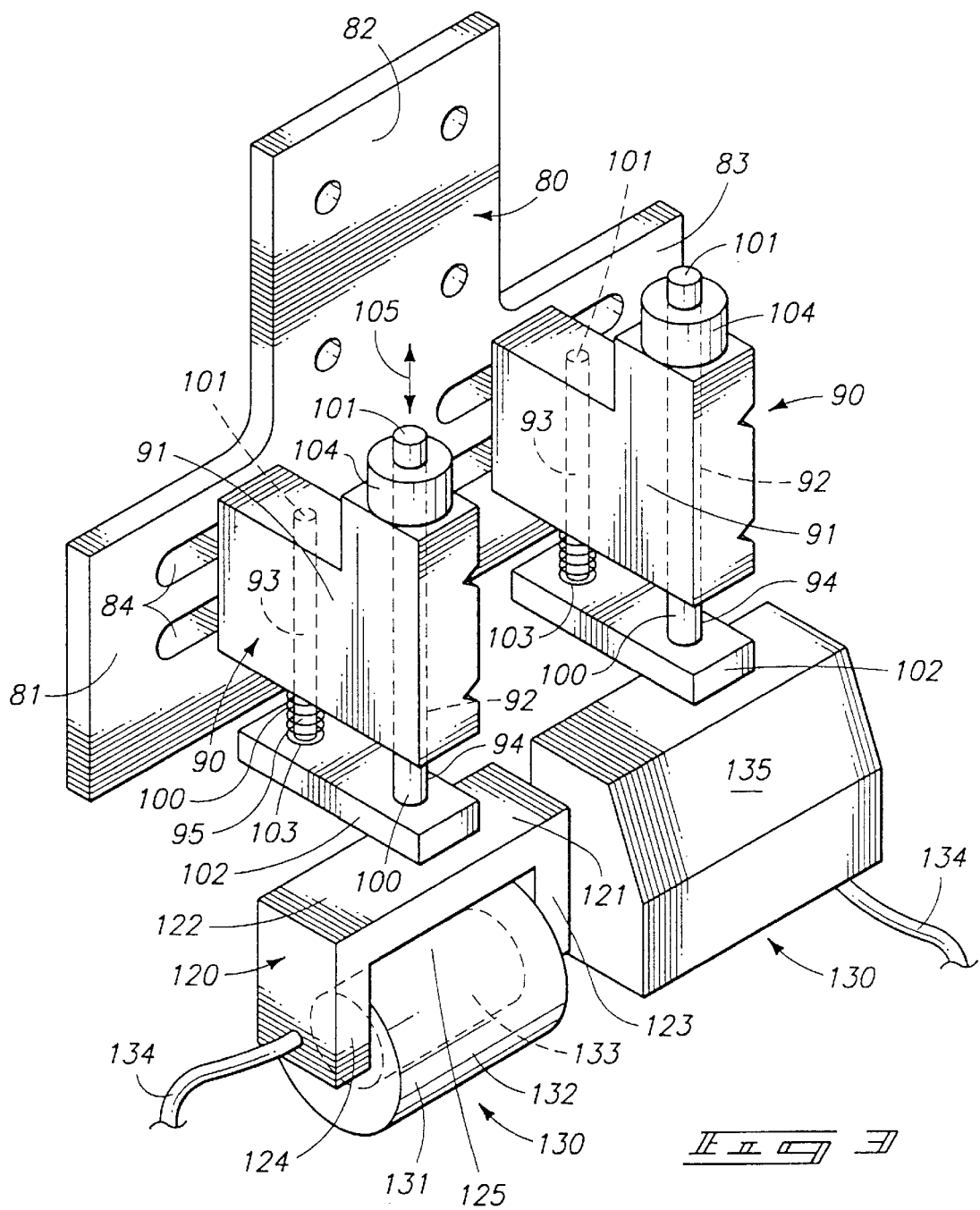

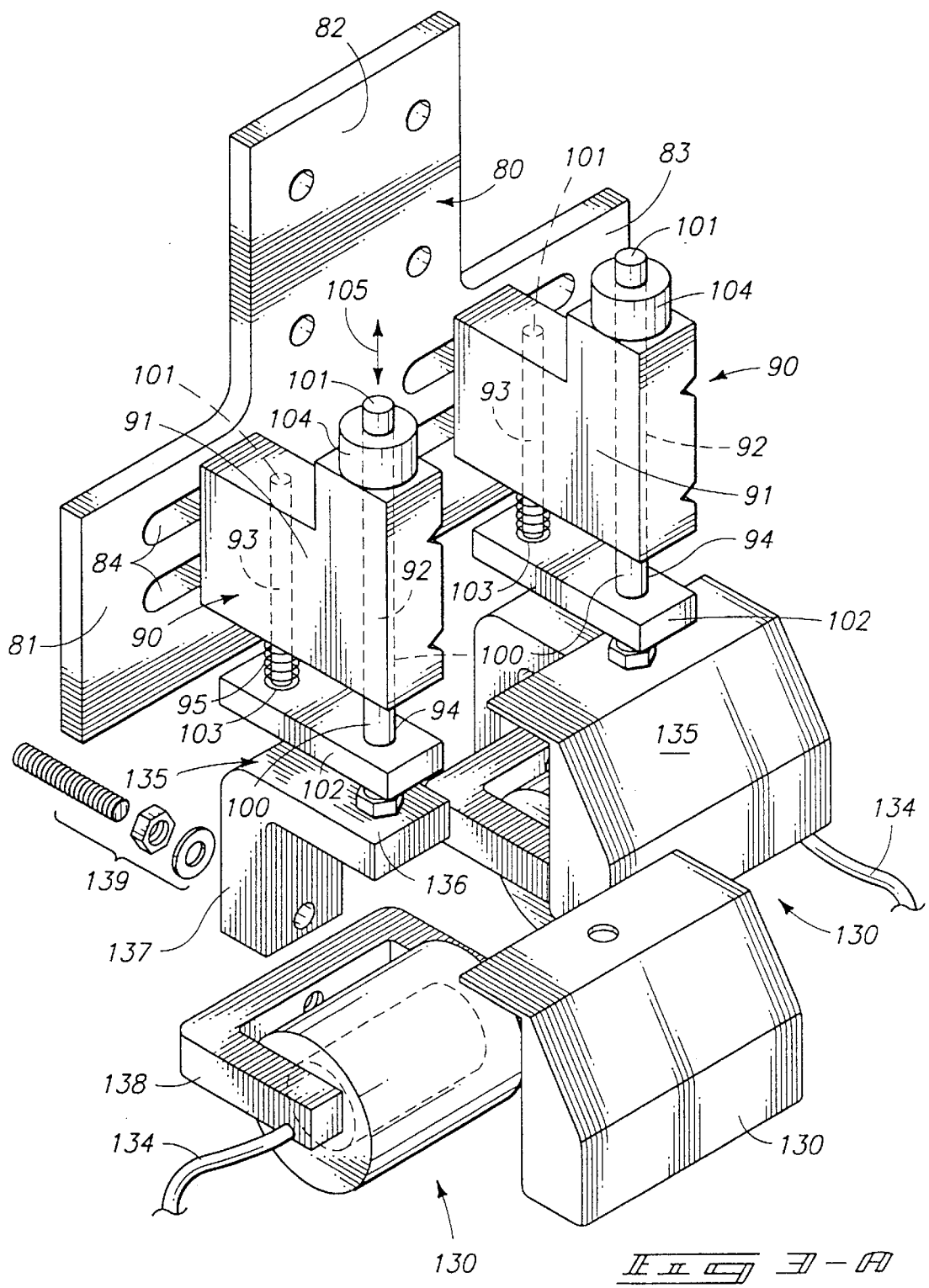

INSPECTION APPARATUS FOR EVALUATING A PARTIALLY COMPLETED WELD

RELATED PATENT DATA

The present application is a continuation in part of U.S. patent application Ser. No. 09/066,723, and which was filed on Apr. 23, 1998 now U.S. Pat. No. 6,125,705.

CONTRACTUAL ORIGIN OF THE INVENTION

The U.S. has rights in this invention pursuant to Contract No. DE-AC07-94ID13223 between the U.S. Department of Energy and Lockheed Martin Idaho Technologies Company.

FIELD OF THE INVENTION

The present invention relates to an inspection apparatus for evaluating partially completed welds and more particularly, to an inspection apparatus which has an ultrasonic sensor which can be optimally adjusted relative to a partially completed weld such that it may effectively inspect the weld to detect welding flaws and advise an operator of same.

BACKGROUND OF THE INVENTION

The prior art is replete with various welding devices which are utilized for joining metal substrates together under various operational and environmental conditions. For example, and as discussed in co-pending application Ser. No. 09/066,723, the inventor has disclosed a technique whereby ultrasonic sensors may be moved generally laterally outwardly relative to the opposite sides of a partially completed weld such that the weld may be thoroughly inspected to determine the presence of assorted welding flaws. In the event that welding flaws are detected, welding operations are normally suspended until the flaw is corrected. This inspection technique greatly facilitates the successful completion of welding operations, while simultaneously reducing the costs of conducting same by substantially reducing time delays normally associated in correcting flaws detected late in the welding process. For example, if a flaw is detected in a given area of the weld once the welding device has passed several times over the same area, significant time delays and expenses are experienced as workers remove the overlying welding material, as by grinding or the like, to uncover the flaw and correct same. The teachings of co-pending application Ser. No. 09/066, 723 and U.S. Pat. No. 4,712,722 which relates to another technique for inspecting partially completed welds are both incorporated by reference herein.

While the prior art devices and methods have operated with varying degrees of success, there have been shortcomings which have detracted from their usefulness. For example, the prior art devices which have been developed have often been difficult or impossible to install on existing welding devices, and once installed, have often been perceived as interfering with some aspects of the welding device's operation. Still further, the often harsh environment in which these welding devices operate have impeded the commercial introduction of same. For example, in welding operations conducted in offshore environments, inspection devices are required to operate on substrates having significant amounts of surface corrosion or scale. In this environment it is often difficult to establish an effective ultrasonic contact with the substrate, or further to confirm the presence of a specific type of welding flaw.

In addition to the foregoing, the prior art devices have been perceived as difficult to operate, and even more difficult to install and maintain.

Therefore, it has long been known that it would be desirable to provide an inspection apparatus for evaluating partially completed welds which provides the benefits which may be derived from related prior art devices and practices, while substantially avoiding the shortcomings, and detriments individually associated therewith.

OBJECTS AND SUMMARY OF INVENTION

Therefore, one aspect of the present invention is to provide an improved inspection apparatus for evaluating a partially completed weld.

Another aspect of the present invention is to provide an inspection apparatus which includes a coupling member, which in one form of the invention, is affixed to an automated movable welder, and which is operable to position the inspection apparatus in an optimal trailing relationship relative to the movable welder.

Another aspect of the present invention is to provide an inspection apparatus which includes a frame member mounting a movable ultrasonic sensor, and a drive assembly which is coupled in driving relation relative to the ultrasonic sensor, and which effectively positions the ultrasonic sensor in an operable location relative to the partially completed weld.

Another aspect of the present invention is to provide an inspection apparatus which includes a coupling member which in one form of the invention effectively permits the ultrasonic sensor to move along a given path of travel into and out of engagement with a supporting surface over which the movable welder operates.

Another aspect of the present invention is to provide an inspection apparatus which includes two ultrasonic sensors which are positioned on the opposite sides of a partially completed weld, and wherein in one first form of the invention, the pair of ultrasonic sensors move in unison together, and in an alternative form of the invention, the two ultrasonic sensors move independently of each other.

Another aspect of the present invention is to provide an inspection apparatus which includes an ultrasonic sensor which is mounted in a rotatable tire and which rests in ultrasonic contact with a supporting surface over which the movable welder operates, and wherein the rotatable tire facilitates the transmission of ultrasonic energy to and from the underlying supporting surface.

Another aspect of the present invention is to provide an inspection apparatus which includes an ultrasonic sensor which is rendered operable to both emit and receive ultrasonic energy.

Another aspect of the present invention is to provide an inspection apparatus which includes a heat dissipation assembly which, in an alternative form of the invention, substantially prevents heat from damaging or impairing the operation of the ultrasonic sensor.

Still another aspect of the present invention is to provide an inspection apparatus which includes a dispenser which, in an alternative form of the invention, applies a material to the ultrasonic sensor to facilitate the transmission of ultrasonic energy to the underlying supporting surface.

Yet, another aspect of the present invention is to provide an inspection apparatus which includes a shield which protects the ultrasonic sensor from damage occasioned by welding debris which is produced during welding operations.

Further aspects and advantages are to provide an improved inspection apparatus for the purposes described and which is economical, reliable, and convenient to operate, and which further avoids the perceived shortcomings associated with the prior art devices and practices.

These and other objectives and advantages are achieved in an inspection apparatus for evaluating a partially completed weld which has opposite sides and which is used in combination with an automated movable welder which moves across a supporting surface comprising:

a coupling member mounted on the welder;

a frame member mounted on the coupling member;

an ultrasonic sensor mounted on the frame member and disposed in ultrasonic sound transmitting relation relative to the partially completed weld; and a drive assembly for adjusting the position of the ultrasonic sensor relative to the partially completed weld.

BRIEF DESCRIPTION OF THE DRAWINGS

FIG. 2 is a partial, perspective, environmental, rear elevational view of one form of the inspection apparatus of the present invention.

FIG. 3 is an enlarged, fragmentary, perspective view of a pair of ultrasonic sensors employed with one form of the present invention. Some surfaces are removed to show the structure thereunder.

FIG. 3A is an enlarged, fragmentary, perspective and exploded view of a pair of ultrasonic sensors employed with an alternative form of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
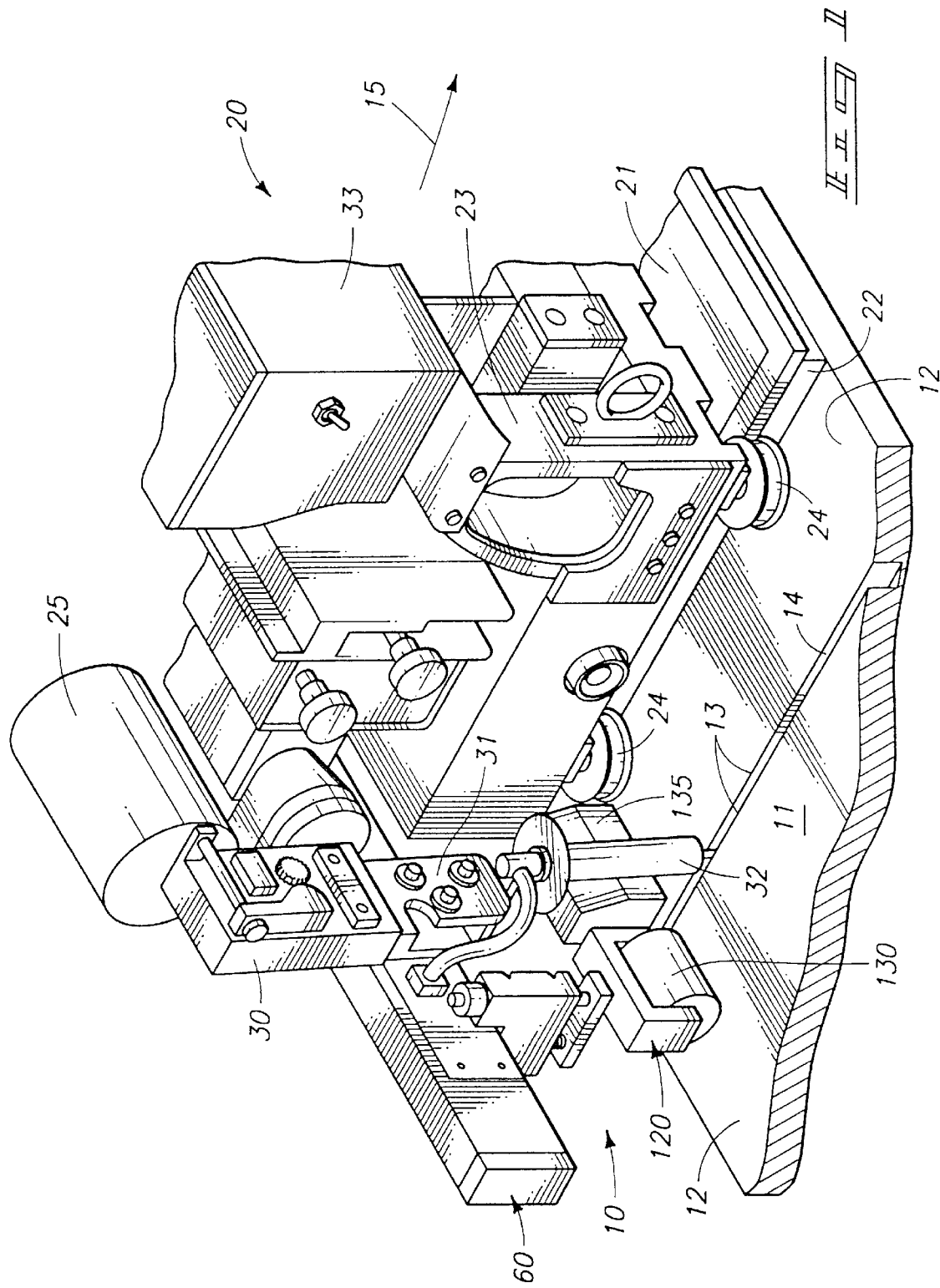
FIG. 1 is a partial, perspective, environmental, frontal elevational view of one form of the inspection apparatus of the present invention.

The inspection apparatus for evaluating a partially completed weld of the present invention is generally indicated by the numeral 10 and is best seen by reference to FIG. 1 and 2, respectively. The inspection apparatus 10 is operable to move across a supporting surface 11, here depicted as a pair of metal plates which are to be subsequently welded together. However, it should be recognized that the invention could be utilized to join metal tubes, pipes or other fabricated shapes. The supporting substrate 11 has a top surface 12 and peripheral edges which are designated by the numeral 13. The peripheral edges as seen in FIG. 2, define a weld joint generally designated by the numeral 14. As seen in FIG. 1, the inspection apparatus 10 is mounted on and disposed in trailing relation relative to the path of travel 15 of an automated movable welder which is generally indicated by the numeral 20.

It should be understood that the automated movable welder 20 is rendered operable to move across the supporting substrate 11 by way of a rail or track 21 which is clamped or otherwise releasably affixed to the underlying supporting substrate 11. The rail or track 21 has a peripheral edge 22. A rack gear (not shown) is mounted along the peripheral edge. The automated movable welder has a carriage 23 which drivingly engages the rail 21 by means of a pinion gear (not shown) and which meshingly couples with the rack gear. Wheels 24 are disposed in rolling engagement with the peripheral edge 22 of the rail 21. The automated movable welder 20 has a feed motor 25 which is operable to substantially continuously supply a wire-like feed stock or electrode wire (not shown) to the automated movable welder 20. Various types of wire feed stock can, of course, be utilized with the automated movable welder. The feed motor 25 is disposed in driving relation relative to a wire feeder 30. In turn, the wire feeder 30 is disposed upstream of a wire straightener 31 which takes the wire feed stock and bends it into a correct orientation such that it may be continuously fed into the welding torch which is generally designated by the numeral 32. The welding torch is connected in fluid flowing relation with a source of suitable welding gases (not shown). The automated movable welder, and more specifically, the carriage thereof 23, mounts a control box 33 which coordinates the speed of operation and other aspects of the movable welder 20 as it moves along the rail 21. The automated movable welder, of course, is normally programmed to make multiple passes along the weld joint 14 in order to fill the weld joint in an appropriate fashion to complete the weld.

Figure 4:
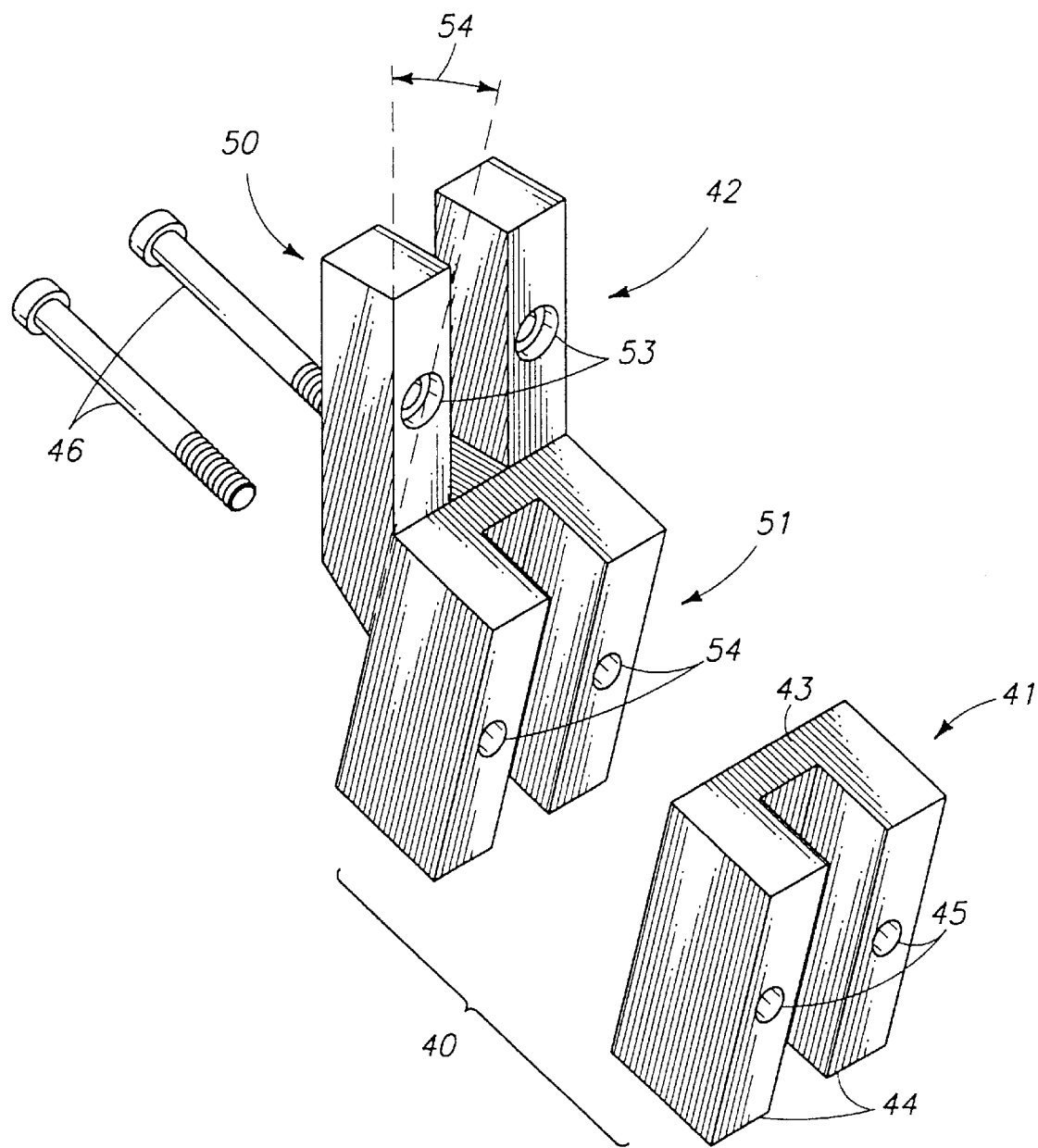
FIG. 4 is a fragmentary perspective, exploded view of one form of a coupler which is employed with the present invention.

As best seen in FIG. 4, a coupler which is generally designated by the numeral 40, releasably affixes the inspection apparatus 10 to the automated movable welder 20. The coupling member or coupler 40 fixes the position of the inspection apparatus 10 in an appropriate and optimal trailing relationship relative to the automated movable welder 20. It should be understood, however, that an alternative form of the coupler may be provided wherein the coupling member defines a path of travel or movement for the inspection apparatus 10. In this regard, this path of travel, which is not shown, would locate or orient the inspection apparatus 10 to permit, on the one hand, the effective ultrasonic inspection of the partially completed weld, and on the other hand, render the inspection apparatus inoperable. Further, the coupling member may be rendered operable to define multiple axes of rotation for the inspection apparatus. By permitting the coupler 40 to define these multiple axes of rotation, the inspection apparatus 10 can be moved to a location where it can be repaired, or replaced or further, provide access to the automated movable welder 20 for purposes of adjustment, maintenance or the like.

It will be recognized by a study of FIGS. 1, 2, and 4, the coupling member 40 places the associated ultrasonic sensor in an operational orientation relative to the supporting surface 11 for transmission of ultrasonic signals in the direction of the partially completed weld. In this regard, the coupling member 40 positions the inspection apparatus 10 in trailing relation relative to the direction of movement of the automated movable welder 20. Still further, the coupling member 40 positions an associated ultrasonic sensor in a substantially optimal spacial relationship relative to one side of the partially completed weld. The ultrasonic sensor, and other aspects of the present invention including the frame member will be discussed in further detail hereinafter.

As seen in the fragmentary exploded view of FIG. 4, the coupler member 40 has first and second portions 41, and 42 respectively. The first portion 41 is mounted on the trailing portion of carriage 23 of the automated movable welder 20.

The first portion 41 comprises a substantially uniformly dimensioned block 43 which is substantially V-shaped in cross section. The block 43 has a pair of legs 44. Individual apertures 45 are formed in each of the legs and are operable to align with threaded apertures which are formed in the carriage 23 of the automated movable welder (not shown). Mounted on the block 43 is the second portion 42. The second portion 42 has a complex shape comprising an upper part 50 and a lower part 51. The upper and lower parts 50 and 51 are substantially unshaped in cross section. Further, a pair of apertures 53, and 54 are formed in each of the upper and lower parts, as shown. As will be appreciated, the apertures 54 which are formed in the lower part are substantially coaxially aligned with apertures 45, when assembled. Fasteners 46 are then received through the coaxially aligned apertures and threadably received in the threaded apertures which are formed in the automated movable welder 20. As best appreciated by a study of FIG. 4, the upper part 50 is oriented relative to the lower part 51 to form an angle which is designated by the numeral 54. This angle is chosen such that rod 94 (which will be subsequently discussed) is substantially perpendicularly oriented relative to the supporting substrate 12. For example, if the device 10 was being utilized to weld substantially flat plates, the angle 54 which would be selected would be zero degrees. However, if the device 10 is being utilized to weld pipe, then an angle would be chosen to achieve the aforementioned objective. As shown in FIG. 4, the second portion 42 has been fabricated for use on surfaces that have a curved geometry, such as a pipe or similar structure.

As best seen in FIG. 2, the inspection apparatus 10 of the present invention includes a frame member which is generally designated by the numeral 60, and which is mounted by means of the coupling member 40 in spaced relation relative to the supporting substrate or surface 11 and in trailing relation relative to the automated movable welder 20. Frame member 60 has a main body 61 which has a first end 62 which is mounted on the second portion 42 of the coupling member 40, and an opposite distal or second end 63 which is remote thereto. Fasteners (not shown) are received in the apertures 53 and threadably engage the main body 60. The main body 61 defines a channel 64 which extends substantially along the longitudinal axis thereof. Mounted on the first and second ends are suitable bearings 65. As seen in FIG. 2, a threaded shaft 70 is received in and is borne by the bearings 65, and is subsequently rendered rotatable thereby. The threaded shaft has a proximal or first end 71, and an opposite, distal or second end 72. Mounted in driving relation relative to the proximal end 71 is a flexible motor coupling 73. Still further, the flexible motor coupling is positioned in force receiving relation relative to an electric motor designated by the numeral 74. Additionally, as seen in FIG. 2, a slidable mounting block 75 is threadably engaged by the threaded shaft 70 and is operable to selectively and reciprocally move along the channel 64. During operation, and upon energizing of the electric motor 74, rotational movement is imparted to the threaded shaft by means of the flexible motor coupling 73. Upon rotation of the threaded shaft, the mounting block 75 moves in a given direction along the channel 64 based upon the direction of rotation (clockwise or counter clockwise) of the threaded shaft. It should be further appreciated, that while one threaded shaft is shown, a pair of threaded shafts 70 could also be provided. Yet further, a second electric motor (not shown) could be provided to power the second shaft for purposes which will be described in greater detail hereinafter. Moreover, it is possible, under certain conditions, that an inspection device 10 may be fabricated whereby a pair of frame members 60 may be utilized as contrasted to the one frame member shown in the drawings. In the present apparatus 10, the drive assembly 77 of same comprises the electric motor 74 which is mounted on the frame 60 and the threaded shaft 70 which is mounted on the frame and disposed in force receiving relation relative to the electric motor.

Affixed on the block 75 is a mounting plate which is generally designated by the numeral 80. The mounting plate 80 has a main body 81 which is substantially T-shaped. In this regard, the main body has a vertically extending portion 82 and a horizontal extending portion attached thereto, and which is designated by the numeral 83. As seen most clearly in FIG. 2, two pairs of substantially parallel oriented slots 84 are formed in the horizontal portion. Furthermore, as seen in FIG. 2, fasteners 85 are threaded through apertures formed in the vertical portion 82 and into the underlying mounting block 75. Additionally, fasteners 86 are received through the parallel slots 84 and are operable to threadably engage a support member, or suspension block 90 which is fastened on the opposite side thereof.

As best seen by reference to FIG. 3, two support members or suspension blocks 90 are shown. Each suspension block 90 has a main body 91 which has first and second passageways 92 and 93 formed therein. As seen in FIG. 3, the diametral dimension of the first passageway 92 is larger than that of the second passageway 93. Slidably mounted in the respective first and second passageways are first and second rods 94 and 95, respectively. Each of the rods have a first or proximal end 100, and an opposite, second or distal end 101. Mounted on the first end 100 of each of the rods 94 and 95 is an arm designated by the numeral 102. Still further, and as seen in FIG. 3, a spring 103 is concentrically received about the second rod 95 and is positioned between the arm and the support member 90. Additionally, a movement limiting assembly 104 is fastened on the distal end 101 of the first rod 94 and is operable to engage the support member 90. In operation, and as best understood by a study of FIGS. 1, 2, and 3, the spring 103 biasingly urges the arm downwardly and into a spaced relationship relative to the suspension block 90. It will be recognized that the respective first and second rods are rendered operable, by means of the spring, for reciprocal movement along path 105 which is seen in FIG. 3.

Affixed to the first end 100 of each of the first rods 94 is a yoke 120. The yoke 120 has a first end 121, and an opposite second end 122. The yoke additionally has first and second legs 123 and 124 which extend substantially, normally, downwardly relative to the respective first and second ends. A gap 125 is defined between the first and second legs 123 and 124. Rotatably mounted in the gap 125 and affixed to the respective first and second legs of each of the yokes 120 is a rotatable tire 130. The rotatable tire has a circumfrential peripheral edge 131 which is fabricated from a synthetic polymeric based material which facilitates the transmission of ultrasonic energy to and from the underlying substrate 11 over which the automated movable welder passes. The rotatable tire defines a cavity 132 in which the ultrasonic sensor 133 is mounted. This cavity is filled with a fluid which facilitates the transmission of ultrasonic energy waves to the peripheral edge 131 and into the supporting substrate 11. As seen in FIG. 3, electrical conduits 134 electrically couple the ultrasonic sensor 133 with an associated analysis assembly which will be discussed in greater detail hereinafter. A fender 135 is mounted on each of the respective yokes 120 (only one of which is shown) and comprises a shield which substantially protects the ultrasonic sensor 133 from any damage which may be occasioned by debris which is produced during welding operations.

Referring now to FIG. 3A, an alternative form of the invention 10 is illustrated and which is useful in supporting the rotatable tire 130 in ultrasonic sound transmitting relation relative to the substrate surface 12. In this regard, the apparatus 10 includes an L-shaped foot 135 which is threadably affixed to the proximal end 100 of the rod 94. the L-shaped foot has a major leg 136, and a minor leg 137 which is disposed at a substantially perpendicular orientation relative thereto. A yoke 138 is affixed by means of a fastener 139 to the minor leg 137. As best seen by comparing the illustration in FIG. 3 and 3A, the yoke 138 is similar in construction to yoke 120, with the exception that yoke 138 is oriented at an angle which is substantially perpendicular to that illustrated for the yoke 120. A fender 130 is releasably affixed to the major leg 136 and operates in a fashion identical to that earlier described. The remaining structure shown in FIG. 3A bears the same numbers, as discussed earlier with respect to the structure shown in FIG. 3, and operates in a similar fashion.

Figure 5:
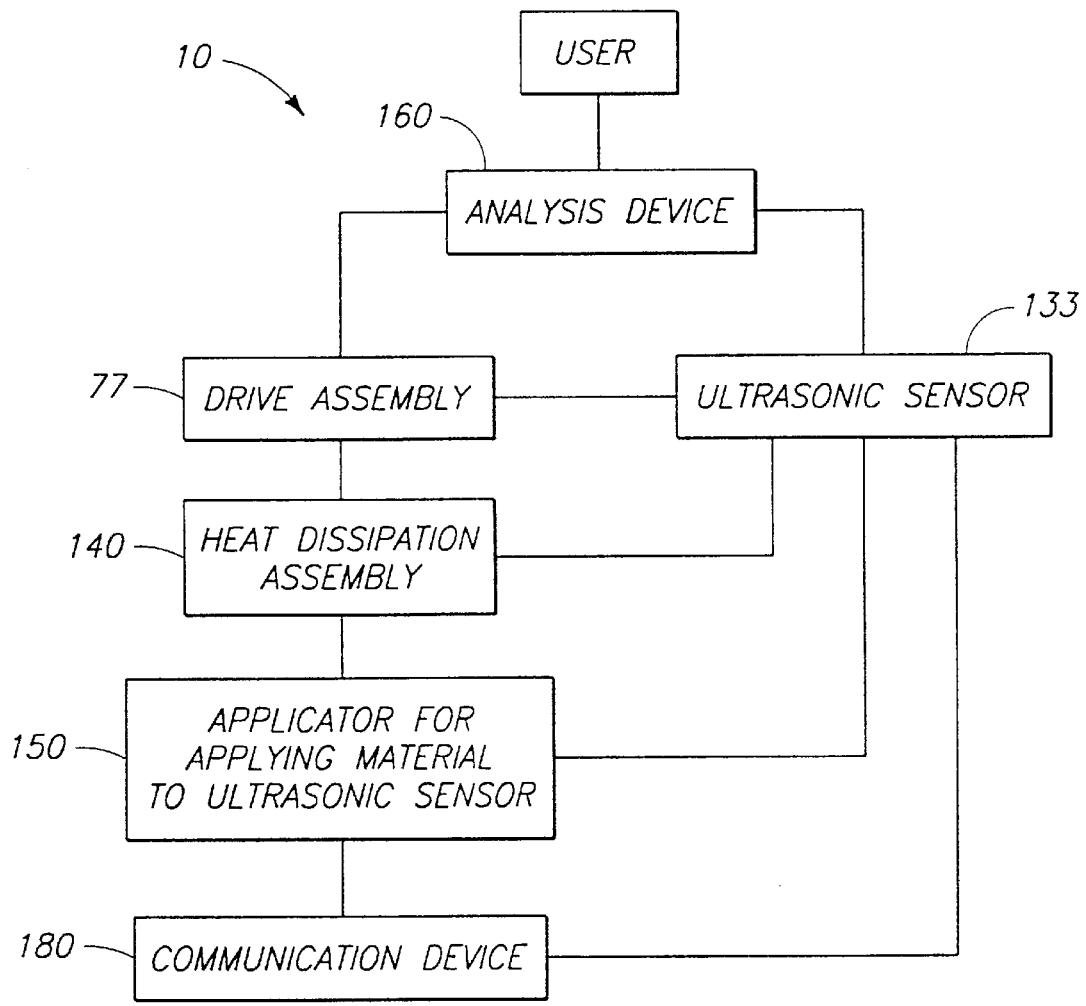
FIG. 5 is a schematic representation of the inspection apparatus of the present invention and showing the relationship of the various components thereof.

In addition to the foregoing, and as best seen by reference to FIG. 5, an optional heat dissipation assembly 140 may be carried by the frame member 60 and which facilitates the dissipation of heat energy from the ultrasonic sensor. Such a heat dissipation assembly may take on various forms, however, its main purpose is to dissipate heat from the rotatable tire 130 thereby preventing damage from occurring to same. This assembly may not be required in all operational environments and is not shown in FIGS. 1 and 2, so as to aid in an understanding of the invention. Also, and as seen in FIG. 5, an optional material dispenser 150 may be carried by the frame 60 and which applies a material to the ultrasonic sensor 133 and more specifically, to the peripheral surface 131 of the rotatable tire 130. This applied material facilitates the transmission of an ultrasonic signal to and from the underlying supporting surface 11. Such material might comprise water or various silicon based gels. These materials would be applied in given amounts to each tire 130 such that good ultrasonic contact would be maintained between the peripheral surface 131 of the rotatable tire 130 and the underlying supporting surface 11. To aid in an understanding of the device 10, the dispenser is not shown in FIGS. 1 and 2.

Figure 6:
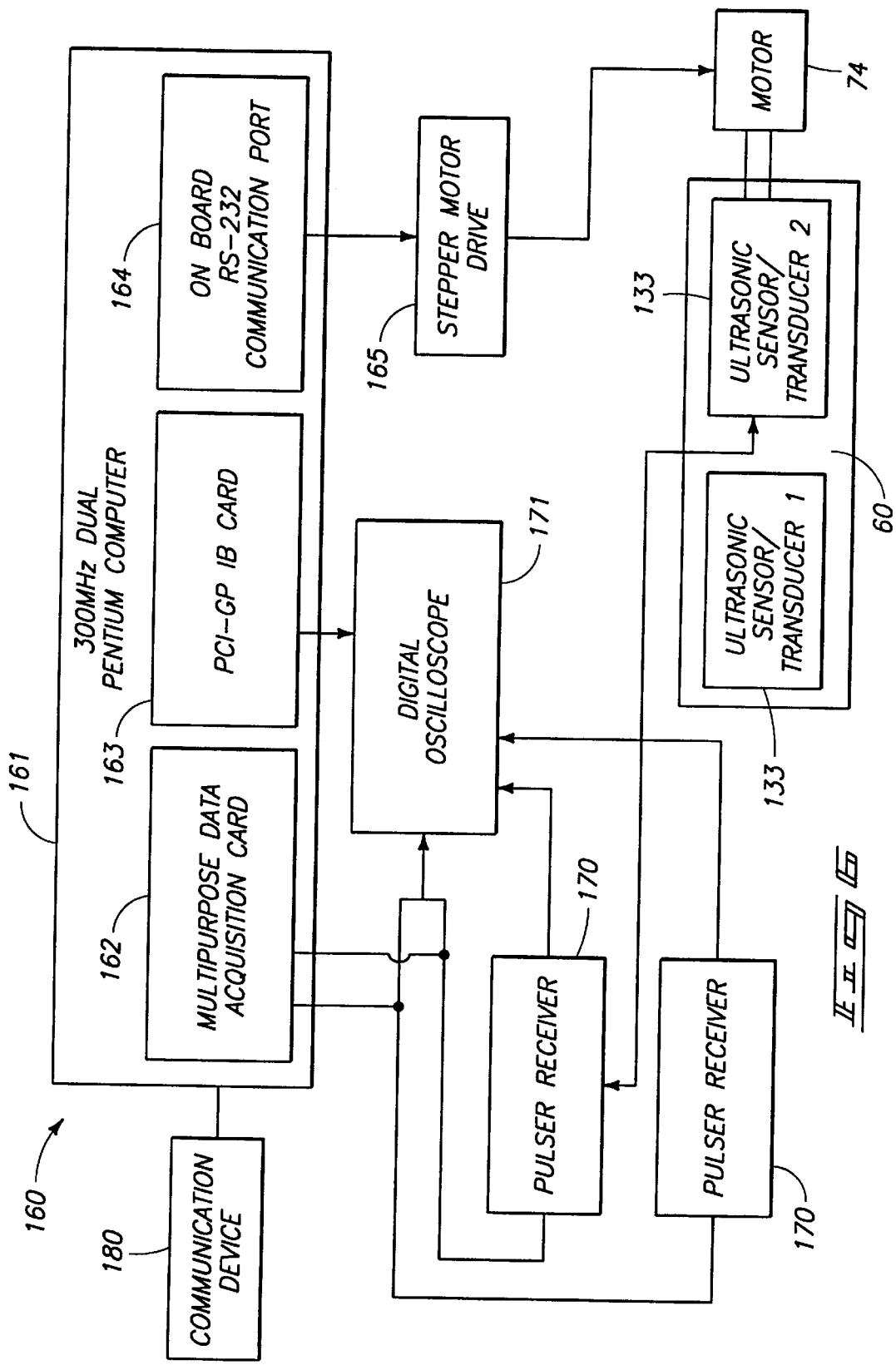
FIG. 6 is a schematic representation of an analysis assembly employed with the present invention.

As seen in FIGS. 5 and 6, the inspection apparatus 10 of the present invention further comprises an analysis assembly which is generally designated by the numeral 160 and which further is electrically coupled with the ultrasonic sensor 133. The analysis assembly 160 interprets the ultrasonic signal received or transmitted by the respective ultrasonic sensors 133 to identify predetermined types of welding flaws. The analysis assembly is best understood by a study of the schematic drawing shown in FIG. 6. As shown therein, the analysis device includes a 300 mhz dual Pentium Computer 161. The Pentium trademark is owned by Intel Corporation. The computer 161 includes a data acquisition card 162, a PCI-GPIB card 163, and a communication port RS-232 164. The computer can be purchased commercially from manufacturers such as Micron as a 300 megahertz dual Pentium computer which has approximately 120 megabytes of RAM installed. The multipurpose data acquisition card may be purchased from National Instruments under the trade designation AT-MI0-16-E-2. Further the PCI-GPIB card may also be purchased from National Instruments. The RS-232 communication port is normally standard on such computers. Electrically coupled with the motor 74 is a stepper motor drive 165. The stepper motor drive is electrically coupled to the communications port 164. Additionally, the analysis device 160 includes a pair of pulsar receivers which are individually coupled to the respective ultrasonic sensors 133. Still further, the device includes a digital oscilloscope 171 which may be purchased from Hewlett Packard under the trade designation 54645A. The pair of pulsar receivers 170 may be commercially purchased from Panametrics under the trade designation 5055PR.

In this arrangement, as shown in the drawings, the data acquisition is done by the digital oscilloscope 171. The digital oscilloscope 171 is a two channel oscilloscope that acquires a signal at about 200 megasamples per second. The digital oscilloscope 171 is provided with the digital outputs of the multipurpose data acquisition card. The digital outputs are tied together by diodes before entering the digital oscilloscope 171, therefore, a pulse on a digital line will trigger only the corresponding pulsar receiver 170, but a pulse on either line will trigger the digital oscilloscope 171. The computer 161 can therefore individually control the pulsar receivers 170 while recording data from either one. As earlier discussed, the ultrasonic sensors 133 are mounted on the frame member 60 and are selectively moved by the motor 74. The motor 74 is, in turn, controlled by the stepper motor drive 165. As noted above, the stepper motor drive is electrically linked to the computer 161 by the RS232 communication port 164. Software is provided for controlling the analysis device 160 as described above. In this regard, the software offers flexibility as to which of the ultrasonic sensors 133 are used in the system, and which ultrasonic signals are received and analyzed. The software (not shown) checks to verify what the user has selected, and then verifies that all configurations are done correctly. Software which is commercially available and which can implement the foregoing can be secured and written in LabView which is a graphical programming language which can be secured from National Instruments. When the analysis assembly is operating effectively, a user can select several ultrasonic transmission and reception configurations. For example, a user can choose to transmit on only one ultrasonic sensor/transducer 133, or on the other one, or can transmit on both. If the user has elected to transmit on both ultrasonic sensor/transducers 133, the computer then toggles transmission between each of the ultrasonic sensors 133. There are four signals that can be received by the system. If an ultrasonic sensor has been pulsed, then one ultrasonic sensor can receive a pulse echo (PE) and the other ultrasonic sensor/transducer 133 can receive a pitch catch signal (PC). Many different variations can be provided. Such is describe in significant detail in the earlier co-pending application which has been incorporated by referenced herein. Still further, the software can be configured to provide various graphical images to provide a graphic user interface for the user of the device 10.

As best seen in FIGS. 5 and 6, the apparatus 10 includes a communication device 80 which provides visual indicia for the user. The visual indicia will give the operator of the device 10 the precise location of the welding flaw and additionally identifies the type of welding flaw at that location. The communication device 180 may provide a printed copy or video display which provides coordinates for locating the welding flaw. Still further, the apparatus 10 may be equipped with an assembly which applies various colored paints to the surface of the supporting substrate 11 which indicates not only the location of the welding flaw but the type of flaw. This may be accomplished by means of spraying the supporting surface 11 with a given color or combination of colors of paint to identify the welding flaw at that location. The communication device is controlled by the computer 161 in response to the analysis done on the ultrasonic signals received and transmitted by the respective ultrasonic sensors transducers 133, respectively.

OPERATION

The operation of the described embodiment of the present invention is believed to be readily apparent and is briefly summarized at this point.

The inspection apparatus 10 for evaluating a partially completed weld which has opposite sides and which is used in combination with an automated movable welder which moves across a supporting surface 11 is best seen in FIGS. 1 and 2. As shown therein, the device 10 includes a coupling member 40 which is mounted on the automated movable welder 20; a frame member 60 mounted on the coupling member 40, an ultrasonic sensor 133 mounted on the frame member 60 and disposed in ultrasonic sound transmitting relation relative to the partially completed weld; and a drive assembly 77 for adjusting the position of the ultrasonic sensor 133 relative to the partially completed weld. As earlier discussed, the coupling member 40, in an alternative form of the invention, may define a path of movement for the frame member 60. Still further, the coupling member 40 as shown positions the ultrasonic sensor 133 in an operational orientation relative to the supporting surface 11 for transmission of ultrasonic signals in the direction of the partially completed weld. Additionally, the coupling member 40 positions the ultrasonic sensor 133 in a substantially optimal spacial relationship relative to one side of the partially completed weld. As earlier discussed, the device 10 may operate with one ultrasonic sensor 133 or as shown herein, with a pair of ultrasonic sensors/transducers which are mounted on the opposite sides of the partially completed weld (FIG. 1). As seen in the drawings, the frame member 60 is mounted in trailing relation relative to the automated movable welder 20 and the drive assembly 77 comprises an electric motor 74 mounted on the frame member 60 and a threaded shaft 70 mounted on the frame member and disposed in force receiving relation relative to the electric motor 74. As noted earlier, in an alternative form of the invention, the drive assembly 77 may comprise a pair of electric motors 74 which are mounted on the frame member 60, and a pair of threaded shafts 70 which are individually disposed in force receiving relation relative to each of the electric motors 74. As shown in FIG. 2, a pair of ultrasonic sensors 133 are mounted on the frame member 60 and are operable to move in unison relative to the partially completed weld. However, as noted above, the device 10 may be rendered operable such that the individual ultrasonic sensors 133 move independently of each other as by a pair of threaded shafts, or by alternative means.

As noted in greater detail earlier in the specification, the automated movable welder 20 produces debris during welding operations and the apparatus 10 further comprises a shield, or fender 135, which is mounted on the frame member 60 and which substantially protects the ultrasonic sensor 133 from the debris produced during welding operations. The device 10 may also include, in an alternative form, a heat dissipation assembly 140 which may be borne by the frame member 60 and which facilitates the dissipation of heat energy from the ultrasonic sensor 133. Still further, the device 10 may also include a material applicator or dispenser 150 which is operable to apply a given material to the ultrasonic sensor 133 to facilitate the transmission of an ultrasonic signal to and from the supporting surface 11. As earlier described, with respect to the analysis device 160, the ultrasonic sensors 133 may be rendered operable to both emit and receive ultrasonic signals. As such, these devices are indicated as an ultrasonic sensor and transducer in FIG. 6.

The subject invention 10 further comprises an analysis assembly 160 which is electrically coupled with the ultrasonic sensors 133 and which interprets the ultrasonic signal received by the respective ultrasonic sensors. The analysis assembly 160 identifies predetermined types of welding flaws. Additionally, a communication device 180 is provided and which is electrically coupled to the ultrasonic sensors and the analysis assembly 160. The communications device identifies the locations and the type of the predetermined welding flaws such that a user or operator of the device 10 may address the specific welding flaws uncovered.

The apparatus 10 more specifically includes a coupling member 40 mounted on the automated movable welder 20, a frame member 60 mounted on the coupling member 40 and disposed in spaced relation relative to the supporting surface 11 over which the automated movable welder 20 moves; a movable support member 90 mounted on the frame member 60; an ultrasonic sensor 133 mounted on the support member 90 and disposed in ultrasonic sound transmitting relation relative to the partially completed weld, and wherein the coupling member 40 orients the ultrasonic sensor 133 in trailing relation relative to the direction of travel of the automated movable welder 20; an analysis assembly 160 electrically coupled with the ultrasonic sensor 133 and which interprets ultrasonic signals received by the ultrasonic sensor 133 to identify predetermined welding flaws; a communications device 160 electrically coupled with the ultrasonic sensor 133, and the analysis assembly 160, the communication device identifying the location and the type of welding flaws; and a drive assembly 77 borne by the frame member 60 for adjusting the position of the ultrasonic sensor 133 relative to the partially completed weld, the drive assembly positioning the movable support member 90 in predetermined locations along the frame member 60.

Therefore, it will be seen that the inspection apparatus 10 of the present invention provides a convenient means whereby a partially completed weld may be effectively inspected during welding operations and in such a fashion whereby welding flaws can be detected easily, efficiently, and economically and in a fashion not possible heretofore.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An inspection apparatus for evaluating a partially completed weld which has opposite sides and which is used in combination with an automated movable welder which moves across a supporting surface, comprising:

a frame member mounted on the welder;

an ultrasonic sensor mounted on the frame member and disposed in ultrasonic sound transmitting relation relative to the partially completed weld; and a drive assembly for concurrently adjusting the position of the ultrasonic sensor relative to the partially completed weld during welding operations and wherein the ultrasonic sensor images the partially completed weld during welding operations.

2. An apparatus as claimed in claim 1, and further comprising a coupling member which releasably affixes the frame member to the welder.

3. An apparatus as claimed in claim 2, wherein the coupling member defines a path of movement for the frame member.

4. An apparatus as claimed in claim 1, wherein the frame member positions the ultrasonic sensor in an operational orientation relative to the supporting surface for transmission of ultrasonic signals in the direction of the partially completed weld.

5. An apparatus as claimed in claim 1, wherein the frame member positions the ultrasonic sensor in a substantially optimal spatial relationship relative to one side of the partially completed weld.

6. An apparatus as claimed in claim 1, wherein the drive assembly is mounted on the frame member.

7. An apparatus as claimed in claim 1, wherein the frame member is mounted in spaced relation relative to the supporting surface, and in trailing relation relative to the automated moveable welder.

8. An apparatus as claimed in claim 1, wherein the drive assembly comprises:

a motor mounted on the frame member; and a threaded shaft mounted on the frame member and disposed in force receiving relation relative to the motor.

9. An apparatus as claimed in claim 1, wherein the drive assembly comprises a pair of motors mounted on the frame member, and a pair of threaded shafts individually disposed in force receiving relation relative to each of the motors.

10. An inspection apparatus for evaluating a partially completed weld which has opposite sides and which is used in combination with an automated movable welder which moves across a supporting surface, comprising:

a frame member mounted on the welder;

an ultrasonic sensor mounted on the frame member and disposed in ultrasonic sound transmitting relation relative to the partially completed weld; and a drive assembly for adjusting the position of the ultrasonic sensor relative to the partially completed weld, and wherein the drive assembly comprises a motor mounted on the frame member, and a threaded shaft mounted on the frame member and oriented in force receiving relation relative to the motor, and wherein energizing the motor imparts rotational movement to the threaded shaft, and wherein the ultrasonic sensor is threadably mounted on the threaded shaft, and rotational movement of the threaded shaft urges the ultrasonic sensor along the frame member.

11. An apparatus as claimed in claim 10, and further comprising a second ultrasonic sensor mounted on the frame member, and wherein the second ultrasonic sensor is disposed in ultrasonic sound transmitting relation relative to the opposite side of the partially completed weld.

12. An apparatus as claimed in claim 10, and further comprising a second ultrasonic sensor mounted on the frame member and disposed in ultrasonic sound transmitting relation relative to the opposite side of the partially completed weld, and wherein the second ultrasonic sensor moves in unison with the first ultrasonic sensor.

13. An apparatus as claimed in claim 10, and further comprising a second ultrasonic sensor mounted on the frame member and disposed in ultrasonic sound transmitting relation relative to the opposite side of the partially completed weld, and wherein the first and second ultrasonic sensors move independently of each other.

14. An apparatus as claimed in claim 10, and further comprising a second frame member, and a second ultrasonic sensor is mounted on the second frame member and disposed in ultrasonic sound transmitting relation relative to the opposite side of the partially completed weld.

15. An apparatus as claimed in claim 10, and further comprising a support member mounted on the frame member and which extends substantially laterally outwardly relative to the frame member, and wherein the ultrasonic sensor is mounted on the support member.

16. An apparatus as claimed in claim 10, and further comprising a support member movably mounted on the frame member and which extends substantially laterally outwardly relative to the frame member, and wherein the ultrasonic sensor is biasingly mounted on the support member.

17. An apparatus as claimed in claim 10, wherein the automated moveable welder produces debris during welding operations, and wherein the apparatus further comprises a shield mounted on the frame member and which substantially protects the ultrasonic sensor from debris produced during welding operations.

18. An inspection apparatus for evaluating a partially completed weld which has opposite sides and which is used in combination with an automated movable welder which moves across a supporting surface, comprising:

a frame member mounted on the welder;

an ultrasonic sensor mounted on the frame member and disposed in ultrasonic sound transmitting relation relative to the partially completed weld;

a drive assembly for adjusting the position of the ultrasonic sensor relative to the partially completed weld; and a heat dissipation assembly borne by the frame member and which facilitates the dissipation of heat energy from the ultrasonic sensor.

19. An apparatus as claimed in claim 18, and further comprising a dispenser borne by the frame member and which applies a material to the ultrasonic sensor which facilitates the transmission of an ultrasonic signal to and from the supporting surface.

20. An apparatus as claimed in claim 18, wherein the ultrasonic sensor is enclosed within a rotatable tire which is mounted on the frame member, and wherein the rotatable tire is in engagement with the supporting surface and further facilitates the transmission of an ultrasonic signal emitted by the ultrasonic sensor to the supporting surface.

21. An apparatus as claimed in claim 18, wherein the ultrasonic sensor operates to both emit and receive ultrasonic signals.

22. An apparatus as claimed in claim 18, wherein the ultrasonic sensor is enclosed within a rotatable tire which is in engagement with the supporting surface, and which further is mounted on the frame member, and wherein the rotatable tire facilitates the transmission of an ultrasonic signal emitted by the ultrasonic sensor to the supporting surface, and wherein the apparatus further comprises a dispenser borne by the frame member and which applies a material to the rotatable tire which facilitates the transmission of an ultrasonic signal to and from the supporting surface.

23. An apparatus as claimed in claim 18, and further comprising a communication device which is electrically coupled with the ultrasonic sensor and which identifies the location and type of predetermined welding flaws.

24. An apparatus as claimed in claim 18, and further comprising an analysis assembly electrically coupled with the ultrasonic sensor and which interprets the ultrasonic signal received by the ultrasonic sensor to identify predetermined types of welding flaws; and a communications device which is electrically coupled with the ultrasonic sensor and the analysis assembly, the communications device identifying the location and the type of the predetermined welding flaws.

25. An apparatus as claimed in claim 18, wherein the apparatus further comprises first and second support members which are mounted on the frame member and which extend outwardly relative to the frame member, and wherein the ultrasonic sensor is mounted on the first support member; and a second ultrasonic sensor is mounted on the second support member; and wherein the drive assembly is borne by the frame member and mounted in force transmitting relation relative to the respective first and second support members to adjustably position the first and second ultrasonic sensors in an optimal orientation relative to the opposite sides of the partially completed weld.

26. An inspection apparatus for evaluating a partially completed weld which has opposite sides and which is used in combination with an automated movable welder which moves across a supporting surface, comprising:
   a frame member mounted on the welder and disposed in spaced relation relative to the supporting surface over which the automated moveable welder moves;
   an ultrasonic sensor movably mounted on the frame member and disposed in ultrasonic sound transmitting relation relative to the partially completed weld, and wherein the frame member orients the ultrasonic sensor in trailing relation relative to the direction of travel of the automated movable welder; and
   a drive assembly borne by the frame and which concurrently adjusts the position of the ultrasonic sensor relative to the partially completed weld during welding operations, and wherein the ultrasonic sensor images the partially completed weld during welding operations.

27. An apparatus as claimed in claim 26, wherein a moveable support member is mounted on the frame member and extends outwardly relative to the frame member, and wherein the ultrasonic sensor is mounted on the support member, and the drive assembly moves the support member along the frame member to optimally position the ultrasonic sensor relative to the partially completed weld.

28. An apparatus as claimed in claim 26, wherein the drive assembly comprises a threaded shaft mounted on the frame member, and a motor mounted on the frame member and which is disposed in force transmitting relation relative to the threaded shaft, and wherein the ultrasonic sensor is mounted on the threaded shaft, and wherein energizing the motor imparts axially oriented rotational movement to the threaded shaft, and wherein rotation of the threaded shaft urges the ultrasonic sensor along the frame member.

29. An apparatus as claimed in claim 26, and further comprising a second ultrasonic sensor mounted on the frame member and disposed on the opposite side of the partially completed weld, and wherein the pair of ultrasonic sensors move in unison together.

30. An apparatus as claimed in claim 26, and further comprising a second ultrasonic sensor movably mounted on the frame member and disposed on the opposite side of the partially completed weld, and wherein the pair of ultrasonic sensors move independently of each other.

31. An apparatus as claimed in claim 26, wherein the automated moveable welder produces debris during welding operations, and wherein the apparatus further comprises a shield mounted on the frame member and which substantially protects the ultrasonic sensor from any welding debris produced during welding operations.

32. An apparatus as claimed in claim 26, and further comprising a heat dissipation assembly borne by the frame member and which facilitates the dissipation of heat energy from the ultrasonic sensor.

33. An apparatus as claimed in claim 26, and further comprising a dispenser borne by the frame member and which applies a material to the ultrasonic sensor which facilitates the transmission of an ultrasonic signal to and from the supporting surface.

34. An apparatus as claimed in claim 26, wherein the ultrasonic sensor is enclosed within a rotatable tire which is mounted on the frame member, and wherein the rotatable tire facilitates the transmission of an ultrasonic signal emitted by the ultrasonic sensor to the supporting surface.

35. An apparatus as claimed in claim 26, wherein the ultrasonic sensor operates to both emit and receive ultrasonic signals.

36. An apparatus as claimed in claim 26, and further comprising a communications device which is electrically coupled with the ultrasonic sensor and which identifies the location and type of predetermined welding flaws.

37. An apparatus as claimed in claim 26, and further comprising an analysis assembly electrically coupled with the ultrasonic sensor and which interprets the ultrasonic signal received by the ultrasonic sensor to identify predetermined types of welding flaws; and a communication device which is electrically coupled with the ultrasonic sensor and the analysis assembly, the communications device identifying the location and the type of predetermined welding flaws.

38. An inspection apparatus for evaluating a partially completed weld which has opposite sides and which is used in combination with an automated movable welder which moves across a supporting surface, comprising:
   a coupling member mounted on the welder;
   a frame member mounted on the coupling member and disposed in spaced relation relative to the supporting surface over which the automated moveable welder moves;
   a moveable support member mounted on the frame member;
   an ultrasonic sensor mounted on the support member and disposed in ultrasonic sound transmitting relation relative to the partially completed weld, and wherein the coupling member orients the ultrasonic sensor in trailing relation relative to the direction of travel of the automated movable welder;
   an analysis assembly electrically coupled with the ultrasonic sensor, and which interprets ultrasonic signals received by the ultrasonic sensor to identify predetermined welding flaws;
   a communication device electrically coupled with the ultrasonic sensor and the analysis assembly, the communication device identifying the location and the type of welding flaw; and
   a drive assembly borne by the frame for concurrently adjusting the position of the ultrasonic sensor relative to the partially completed weld during welding operations the drive assembly positioning the moveable support member in predetermined locations along the frame member, and wherein the ultrasonic sensor images the partially completed weld during welding operations.

39. An apparatus as claimed in claim 38, wherein the automated moveable welder produces debris during welding operations, and wherein the apparatus further comprises a shield mounted on the frame member and which substantially protects the ultrasonic sensor from any debris produced during welding operations.

40. An apparatus as claimed in claim 38, and further comprising a heat dissipation assembly borne by the frame member and which facilitates the dissipation of heat energy from the ultrasonic sensor.

41. An apparatus as claimed in claim 38, and further comprising a dispenser borne by the frame member and which applies a material to the ultrasonic sensor which facilitates the transmission of an ultrasonic signal to and from the supporting surface.

42. An apparatus as claimed in claim 38, wherein the ultrasonic sensor is enclosed within a rotatable tire which is mounted on the support member, and wherein the rotatable tire facilitates the transmission of an ultrasonic signal emitted by the ultrasonic sensor to the supporting surface.

43. An apparatus as claimed in claim 38, wherein the ultrasonic sensor operates to both emit and receive ultrasonic signals.

44. An apparatus as claimed in claim 38, and further comprising a second ultrasonic sensor which is movably mounted on the frame member, and wherein the pair of ultrasonic sensors move in unison together.

45. An apparatus as claimed in claim 38, and further comprising a second ultrasonic sensor movably mounted on the frame member, and wherein the pair of ultrasonic sensors move independently of each other.

46. An inspection apparatus for evaluating a partially completed weld which has opposite sides and which is used in combination with an automated movable welder which moves across a supporting surface, comprising:

a coupling member mounted on the welder;

a frame member mounted on the coupling member and disposed in spaced relation relative to the supporting surface over which the automated moveable welder moves;

a rotatable tire movably mounted on the frame member;

an ultrasonic sensor enclosed within the rotatable tire and disposed in ultrasonic sound transmitting relation relative to the partially completed weld, and wherein the coupling member orients the ultrasonic sensor in trailing relation relative to the direction of travel of the automated movable welder;

an analysis assembly electrically coupled with the ultrasonic sensor, and which interprets ultrasonic signals received by the ultrasonic sensor to identify predetermined welding flaws;

a communications device electrically coupled with the ultrasonic sensor and the analysis assembly, the communications device identifying the location and the type of welding flaw; and a drive assembly mounted on a frame member and which concurrently adjusts the position of the ultrasonic sensor relative to the partially completed weld during weld operations, and wherein the ultrasonic sensor images the partially completed weld during welding operations.

47. An apparatus as claimed in claim 46, wherein the automated moveable welder produces debris during welding operations, and wherein the apparatus further comprises a shield which substantially protects the tire from any debris produced during welding operations.

48. An apparatus as claimed in claim 46, and further comprising a heat dissipation assembly borne by the frame member and which facilitates the dissipation of heat energy from the rotatable tire.

49. An apparatus as claimed in claim 46, and further comprising a dispenser borne by the frame member and which applies a material to the rotatable tire which facilitates the transmission of an ultrasonic signal to and from the supporting surface.

50. An apparatus as claimed in claim 46, and further comprising a second rotatable tire movably mounted on the frame, and a second ultrasonic sensor enclosed with the second rotatable tire, and wherein the first and second ultrasonic sensors move in unison with each other.

51. An apparatus as claimed in claim 46, and further comprising a second rotatable tire movably mounted on the frame, and a second ultrasonic sensor enclosed with the second rotatable tire, and wherein the first and second ultrasonic sensors move independently of each other.

* * * * *